(12) United States Patent
Aboul-Hosn et al.

(10) Patent No.: US 6,287,319 B1
(45) Date of Patent: Sep. 11, 2001

(54) CANNULA WITH BALLOON TIP

(75) Inventors: Walid N. Aboul-Hosn; William R. Kanz; Eloy T. Padilla, all of Sacramento, CA (US); Terry M. Wonder, Salt Lake City, UT (US)

(73) Assignee: Amed Systems, Inc., West Sacramento, CA (US)

( * ) Notice: Subject to any disclaimer, the term of this patent is extended or adjusted under 35 U.S.C. 154(b) by 0 days.

(21) Appl. No.: 09/280,987

(22) Filed: Mar. 30, 1999

(51) Int. Cl.[7] ................................................. A61M 29/00
(52) U.S. Cl. ................................................. 606/192
(58) Field of Search ................................. 606/192, 191, 606/194, 158; 604/912, 284, 49, 4

(56) References Cited

U.S. PATENT DOCUMENTS

| 4,508,535 | | 4/1985 | Joh et al. . | |
| 5,135,535 | * | 8/1992 | Kramer | 606/194 |
| 5,160,321 | * | 11/1992 | Sahota | 604/96 |
| 5,435,308 | | 7/1995 | Gallup et al. . | |
| 5,755,687 | | 5/1998 | Donlon . | |
| 5,762,624 | * | 6/1998 | Peters | 604/4 |
| 5,797,948 | | 8/1998 | Dunham . | |

FOREIGN PATENT DOCUMENTS 0 280 225   8/1998   (EP) .

* cited by examiner

Primary Examiner—Henry J. Recla
Assistant Examiner—Vy Q. Bui
(74) Attorney, Agent, or Firm—Jonathan Spangler

(57) ABSTRACT

A cannula is provided with a balloon tip at an implantable end thereof. The balloon tip comprises a sealed, flexible, inflatable portion adapted to receive an inflating material via a lumen in fluid communication therewith. The lumen comprises a gap formed in the tubular wall of the cannula, and may be defined by a supply tube disposed within the lumen and extending between an inflatable material source and the balloon tip.

3 Claims, 5 Drawing Sheets

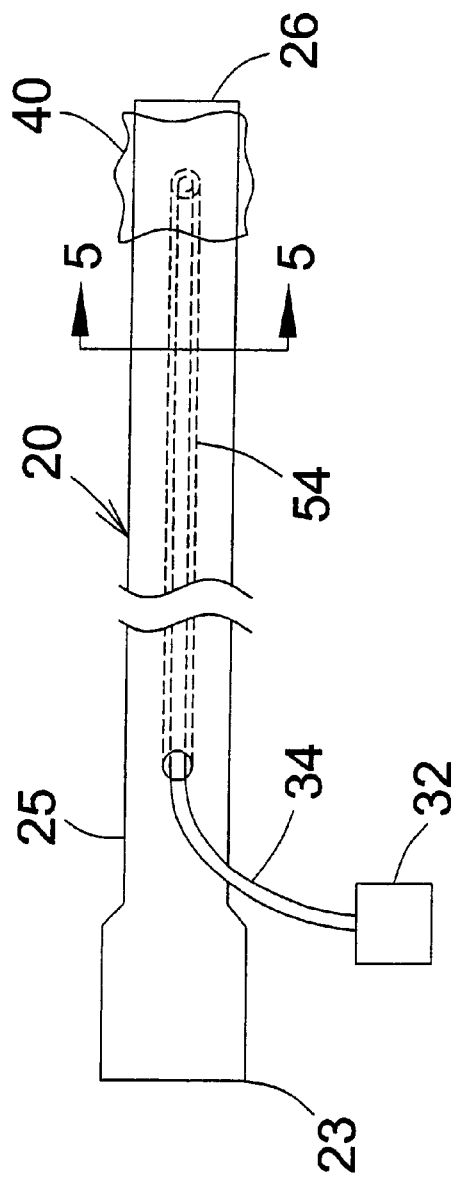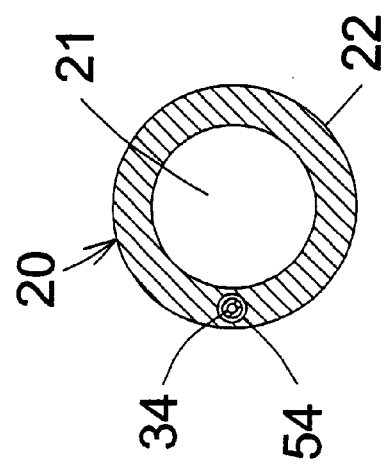

CANNULA WITH BALLOON TIP

BACKGROUND OF THE INVENTION

1. Field of the Invention

The present invention relates to cannulas used in surgical applications, and more particularly, to systems used in guiding such cannulas to the surgical field within the body of a patient.

2. Description of Related Art

In medical applications and specifically in surgery, the list of uses for cannulas is exhaustive. One application involves the augmenting or supplementing of pulmonary blood flow through the beating heart during heart surgery by use of one or more cannulas involved in the intake and return of blood into the circulatory system. The cannulas interface between the patient's circulatory system and the mechanical pumps that power the augmentation process. Such an application is described in co-pending PCT Application No. PCT/US97/18674 entitled "Single Port Cardiac Support Apparatus", filed Oct. 14, 1997 and incorporated herein by reference in its entirety.

Typically, placement of the cannula at the desired location within the patient's body is facilitated by use of guiding devices such as a guide wire threaded through the cannula. The guide wire is easier to manipulate than the cannula, and its placement precedes placement of the cannula. After the guide wire is in place, the cannula is pushed along the length of the guide wire, following the guide wire to the desired destination.

It is also known that a balloon catheter can be used as a guide wire. Balloon catheters are well known in the art and have a multitude of uses, including delivery or removal of fluid from the surgical site. However, balloon catheters are typically at least an order of magnitude smaller than cannulas. Their small size accordingly severely limits their application since both quantity and rate of fluid flow through the catheter are limited. In fact it is precisely because of their small size that balloon catheters can be used as guiding devices for the larger, more robust and versatile cannulas. During use as a guiding device for a cannula, the balloon catheter acts as a guide wire in facilitating the advancement of the cannula to the desired destination. The balloon catheter is first inserted into a desired position within the patient's body, then the cannula is inserted over the balloon catheter, and then advanced into the desired position.

Insertion of the balloon catheter is effected using the inflatable balloon disposed at a distal tip of the balloon catheter. A lumen in communication with the balloon delivers inflating fluid to the balloon, thereby inflating the balloon and causing it to operate as a "sail" which is pulled along in the blood stream through the natural blood flow in the patient's circulatory system.

Further the cannula may be inserted within the patient's body without the aid of any external guiding means. However, this method may be unsatisfactory because the cannula may not be placed properly within the patent's body, thereby causing tissue damage.

Use of guiding devices in the placement of cannulas is particularly unsatisfactory because of the risk of injury to the delicate tissues, especially when the guiding device is withdrawn. The problem is particularly acute when the delicate aortic or pulmonary semilunar valves are involved, restricting the ability to cannulate some portions of the heart during cardiac surgery. Additionally, the process of inserting the guiding device prior to insertion of the cannula requires monitoring of the guiding device in its progress, typically using X-rays. Incident to X-ray use are inherent risks and constraints, and in emergency situations X-ray equipment may not be available at all, or its use may introduce prohibitive time delays.

Moreover, reliance on balloon catheters or other guiding devices for cannula placement introduces a series of additional steps to the cannulation procedure. Since time is critical during surgical applications and the need to minimize the chances of complications of paramount importance, there is a long felt need for a system in which cannulation is effected in a rapid and efficient manner.

SUMMARY OF THE INVENTION

The present invention overcomes the deficiencies of the prior art by providing a cannula having an integrated balloon tip formed at an implantable portion thereof. The balloon tip comprises a balloon in communication with a lumen which is used to transfer inflating material to and from the balloon. When the balloon is inflated, it behaves as a "sail" and is propelled by the patient's natural blood flow to the desired destination in the patient's circulatory system.

The balloon can be formed as a separate tubular structure sealed at its periphery against the exterior of the cannula wall. A supply tube feeds into the balloon, the supply tube being alternatively contained within the wall of the cannula or extending along the interior or exterior thereof.

The balloon can be formed as a pocket between inner and outer layers of the cannula wall, with one of these layers, preferably the inner layer, extending beyond the other layer and folding back and bonding with the other layer to form the pocket. The resilient material of the folded layer thus serves to expand when the pocket is inflated.

One advantage of the arrangement in accordance with the invention is a reliable traverse of the aortic arch or other arteries. During passage through the aortic valve, for example, if the valve is open, the ability to float the tip of the cannula within the fluid stream causes the tip of the cannula to pass through the aortic valve as the cannula is pushed through. If the valve is closed, or if the tip is substantially off center, the balloon when inflated will float the cannula, moving the tip away from the sinus of the aortic valve. The tip then becomes entrapped in the fluid flow, moving the cannula until the pressure is equal about the balloon, thereby centering the tip within the fluid stream. The cannula can then be pushed through the aortic valve when the valve opens.

The invention also permits the user to place the cannula antegrade of a stream of flow, inflate the balloon and allow the fluid to pull the cannula with the flow. In this manner the cannula becomes self-placing within the flow.

The invention also allows the user to "wedge" the cannula within the patient's pulmonary artery to monitor the left arterial pressure, via the pressure sensing tip of the cannula.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 4 is a schematic side view of a cannula having a balloon tip in accordance with a second embodiment of the invention;

FIG. 5 is a schematic cross-sectional view taken along line 5—5 of FIG. 4;

DETAILED DESCRIPTION OF THE PREFERRED EMBODIMENTS

In accordance with the invention, a cannula comprising a substantially tubular, semi-flexible material adapted for fluid transport while inserted in a patient's body is provided with an inflatable balloon at a distal end thereof. The balloon is selectively inflated in order to facilitate insertion of the cannula in the desired location in the patient's body. The balloon acts as a "sail" and is propelled to its destination by circulation of the blood. At its proximal end the cannula is open and is adapted for attachment to various types of secondary tubing. The secondary tubing connects the cannula to any desired equipment.

Figure 1:
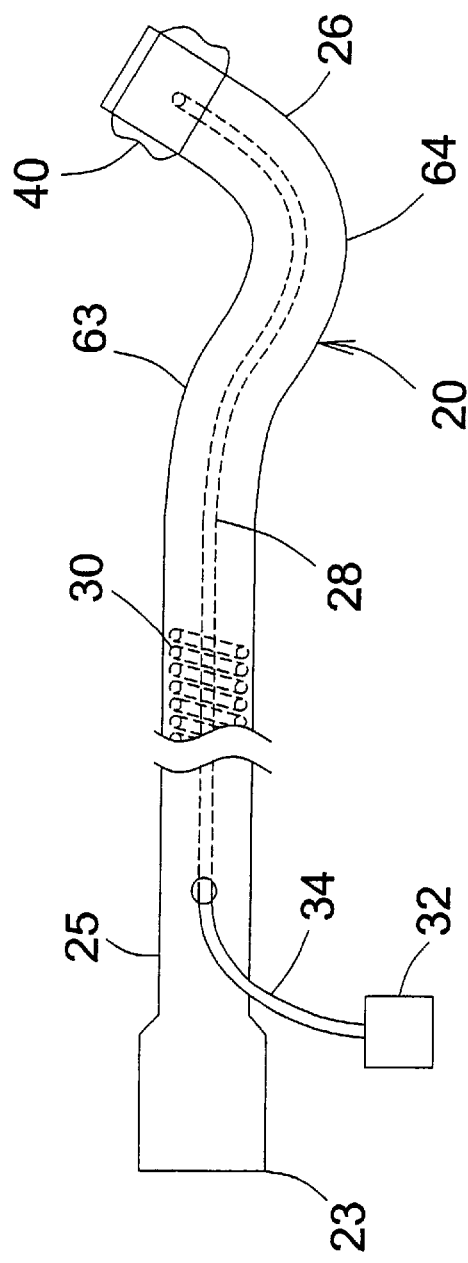
FIG. 1 is a schematic side view of a cannula having a balloon tip in accordance with a first embodiment of the invention, with the balloon in the deflated position
Figure 2:
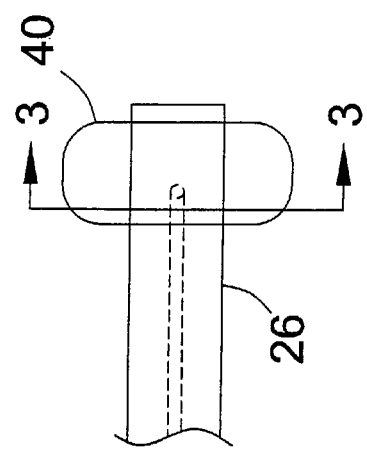
FIG. 2 is a schematic partial side view of a cannula having a balloon tip in accordance with the invention, with the balloon in the inflated position.
Figure 3:
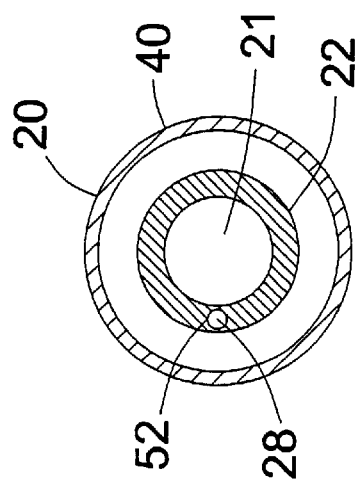
FIG. 3 is a schematic cross-sectional view taken along line 3—3 of FIG. 2.

An exemplary arrangement in accordance with the preferred embodiment of the invention is shown FIGS. 1–3. Cannula 20 comprises a substantially cylindrical structure having a wall 22 defining a main lumen 21. Wall 22 is tubular in shape and can be formed of materials ranging from rigid to flexible, and in the preferred embodiment comprises a semi-rigid transparent material such as polyurethane, silicone rubber or other material. The cannula may further be constructed having varying wall thickness along the length of the cannula. This may be achieved by employing material having various densities which may further enhance the flexibility or stiffness of the cannula. Lumens other than main lumen 21 may also be provided, as described below. Additionally, preformed curves 63, 64 may be provided along the length of cannula 20 in one or more planes. The preformed curve serves to facilitate manipulation of the cannula, especially around tortuous bends during insertion of the cannula in the patient's circulatory system.

To lend structural support, spiraling wire 30 may be provided for reinforcement and is either molded into the wall 22 or is otherwise supported therein, and extends either partially or fully across the length of the cannula 20. Wire 30 facilitates handling of the cannula 20 and reduces the possibility of cannula 20 collapsing or being pinched shut and thus closing off the flow of fluid to or from the patient. Further, by employing wire 30, cannula 20 may be constructed of thin wall tubing having sufficient compressive and hoop strength, thereby maximizing the flow through the cannula. Other ways of reinforcing the tubular body of cannula 20 are known in the art and will adapt equally well to the present invention. In addition, no reinforcement may be needed if the cannula material is sufficiently rigid or if sufficient fluid flow is present within the cannula.

A connector 23 is provided at the proximal end 25 of cannula 20. Connector 23 is suitably sized to interface with various surgical devices, including but not limited to a reverse flow pump or fluid conduits leading thereto (not shown). Cannula 20 may also have one or more holes located adjacent to distal tip 22 to facilitate fluid flow therethrough. Cannula 20 may be one of two complementary cannulas used in a surgical procedure, one for intake and the other for removal of blood or other fluid from the patient's body. Alternatively, cannula 20 may comprise a component of a co-axial, single port device in which cannula 20 is surrounded by a second, larger conduit, with cannula 20 for example operating to outlet blood to the patient from a pump system and the outer conduit operating to intake blood from the patient toward the pump system for augmentation of blood flow during beating heart surgery as described in the co-pending PCT Application No. PCT/US97/18674.

Cannula 20 is also provided at its distal end 26 with a balloon 40, shown in deflated form in FIG. 1 and in inflated form in FIG. 2. Balloon 40 is in communication with a lumen 28 through which inflating material is provided from an inflating material source 32. Such a material may comprise any bio-compatible fluid such as for example saline or carbon dioxide gas. The source 32 may comprise a standard syringe which is used to inject the material into the lumen 28.

Lumen 28 is formed in wall 22, specifically in a gap 54 extending axially along the length of the cannula 20 in parallel relation with main lumen 22. At the proximal end 25 of cannula 20, lumen 28 is in fluid communication with a supply tube 34 for providing inflating fluid to or from source 32. Alternatively, lumen 28 may be defined by the supply tube 34 itself, wherein supply tube 34 extends from source 32, through gap 54, to balloon 40 as shown in FIGS. 4 and 5. Of course, supply tube 34 need not be supported in a gap 54, but can extend interiorly or exteriorly of cannula 20 for fluid delivery between source 32 and balloon 40. Gap 54 is formed in wall 22 and is constructed during the manufacturing process of the cannula 20 by for example leaving an appropriate space between layers comprising wall 22 during the layering process utilized in making the cannula.

Gap 54, may further be formed in wall 22 during the manufacturing process of the cannula 20 by, for example, leaving an appropriate void within the wall 22 during the extrusion process utilized to make the cannula.

Figure 6:
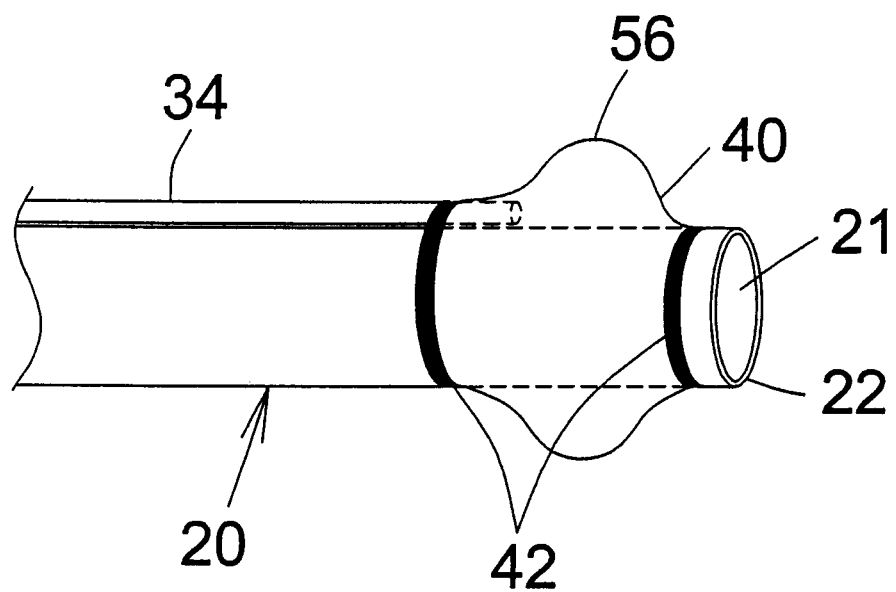
FIG. 6 is a schematic partial perspective view of a cannula tip in accordance with a third embodiment of the invention.

In the FIG. 6 embodiment, balloon 40 is constructed of a resilient, flexible material 56, such as latex, silicon or urethane, sealed at its periphery against wall 28 of cannula 20. The sealing can be effected using heat bonding and/or any suitable adhesive, for example, applied at sealing regions 42. Supply tube 34 penetrates into the region between material 56 and wall 22, preferably under the sealing region 42 as shown.

Figure 7:
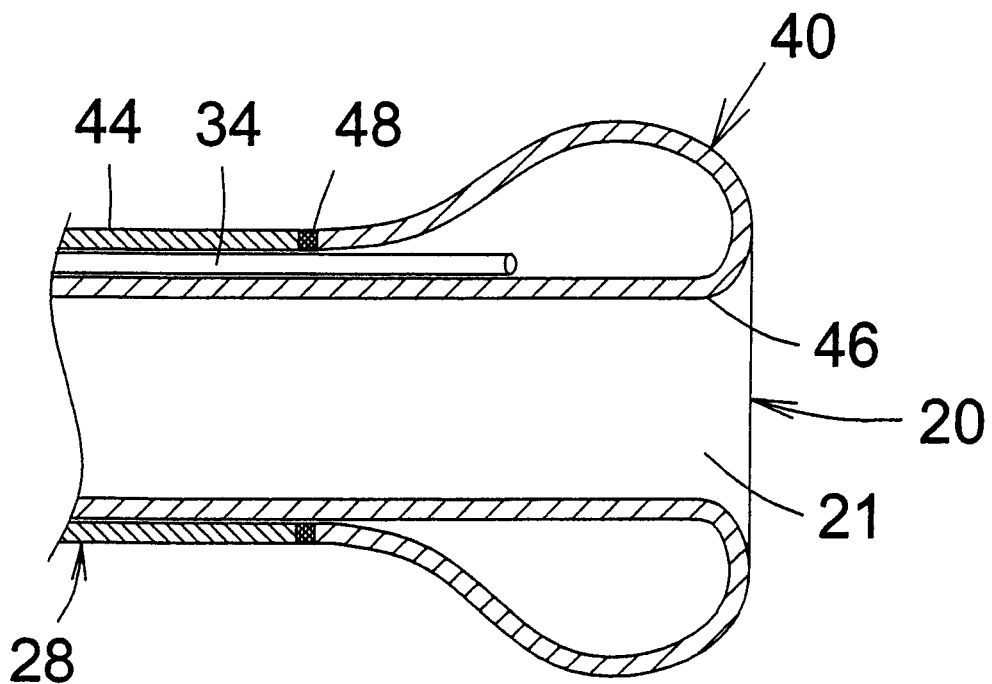
FIG. 7 is a schematic, partial, sectional view of a cannula tip in accordance with a fourth embodiment of the invention.

A second construction for balloon 40 is shown in FIG. 7 and relies on the layered construction of the cannula 20. In this configuration, an inner wall portion 46 of wall 28 is folded outward and sealed against an outer wall portion 44 to thereby form a fluid-tight, unbonded pocket which comprises balloon 40. Portions 44 and 46 may be of different materials to prevent their bonding together. Sealing is effected using for example heat bonding and/or adhesive at region 48. Supply tube 34 feeds into this pocket by passing between portions 44 and 46, although this is not a strict requirement and other ways of supplying balloon 40 with inflating material are contemplated.

In operation, balloon 40 in the deflated configuration lies flush against the surface of cannula 20 in order to reduce turbulence, but increases in size and surface area when inflated for enhanced interaction with the surrounding fluid.

The tip of the cannula 20 becomes suspended in the fluid, floating the cannula to the desired destination.

Various distal tip configurations can be selected for cannula 20, depending on the particular application as appreciated by those of ordinary skill in the art. For example, in addition to the above-illustrated blunt shape, a pigtail shape and a beveled shape are also contemplated, depending on the application.

Figure 8:
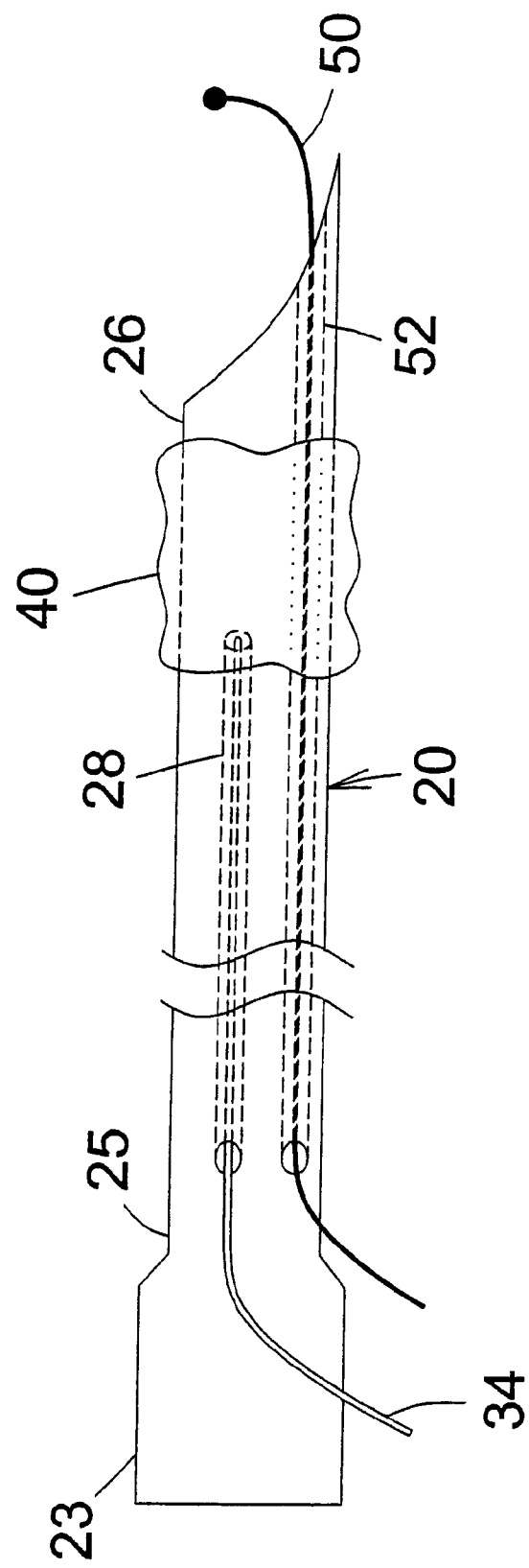
FIG. 8 is a schematic side view of a cannula in accordance with a fifth embodiment of the invention.

As shown exemplarily in FIG. 8, cannula 20 may be equipped to support tools such as a guide wire 50 slidingly or fixedly mounted in a dedicated secondary lumen 52 provided in or attached to wall 22. Lumen 52 is open at proximal end 25 and distal end 26 of cannula 20 and slidingly supports guide wire 50 therein. Guide wire 50 may be provided with one or more permanent bends along its length to aid in its manipulation through the patient's circulatory system. In addition to lumens 28 and 52, other lumens (not shown) can be provided for supporting other equipment such as for example pressure or optical sensors, light projecting light guides for aiding in guidance of cannula 20 through the body. Additionally, other lumens can be provided for dispensing medication or other fluid, or for removing fluids from the body of the patient. Finally, it is contemplated that cannula 20 can be provided with more than one balloon 40 depending on the application.

Figure 9:
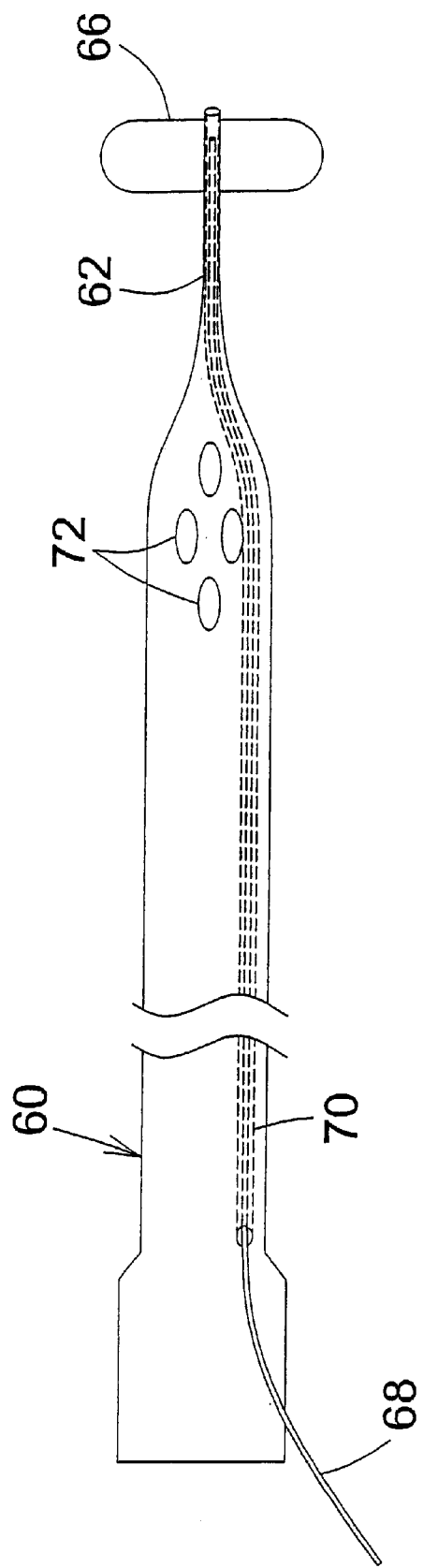
FIG. 9 is a schematic side view of a cannula in accordance with a sixth embodiment of the invention.

FIG. 9 illustrates an arrangement in which the cannula 60 is provided with a balloon 66 formed on a distal tip portion 62 which is substantially smaller in diameter than the main body of the cannula 60. In this manner, distal tip portion 62 is of a significantly small size in relation to the diameter of inflated balloon 60, disposed radially and adjacent to tip portion 62. Advantages of such a design include providing balloon 60, when inflated, with the greatest surface area within the blood flow as possible, thereby maximizing the ability to place the cannula at a desired position within the patient. As seen from the drawing figure, balloon 60 is inflated using for example a tube 68 in fluid communication therewith, the tube 68 being disposed in a lumen 70 provided in the cannula 60.

The above are exemplary modes of carrying out the invention and are not intended to be limiting. It will be apparent to one of ordinary skill in the art that modifications thereto can be made without departure from the spirit and scope of the invention as set forth in the following claims. It will also be apparent that all devices and methods herein disclosed will adapt equally to animal use as well as human use.

What is claimed is:

1. A cannula apparatus, comprising:

a bio-compatible structure having a cannula portion and a guide catheter portion, said guide catheter portion having a substantially smaller diameter than the diameter of the cannula portion;

said cannula portion having a proximal flow port formed in a proximal end thereof, a distal flow port formed in distal end thereof, and a non-apertured region extending between said proximal and distal flow ports, said cannula portion defining a blood flow lumen extending between said proximal and distal flow ports, said non-apertured region enabling continuous and leak-proof transmission of blood between said proximal and distal flow ports;

said guide catheter portion having an inflatable balloon mounted on a distal end thereof, a balloon inflation lumen disposed therein for delivery of inflating fluid from a fluid source to the inflatable balloon, and a closed distal end to prevent blood flow through said guide catheter portion; and said inflatable balloon being dimensioned to have a diameter, when fully inflated, less than a diameter of a blood vessel or heart chamber through which the inflatable balloon is to be passed, such that said balloon may be inflated following insertion into the body to act as a sail within the blood stream and thus facilitate placement of said cannula portion at a location within the body.

2. The cannula apparatus of claim 1, wherein said balloon inflation lumen is formed within a side wall of said bio-compatible structure and extends from said cannula portion into said guide catheter portion for fluid communication with said inflatable balloon.

3. The cannula apparatus of claim 1, wherein said distal flow ports of said cannula portion are formed adjacent to the proximal end of said guide catheter.

* * * * *